United States Patent [19]

Holloway et al.

[11] Patent Number: 5,201,893
[45] Date of Patent: Apr. 13, 1993

[54] IRRIGATION CONTAINER AND SYRINGE

[75] Inventors: Joan M. Holloway, Bartlett; Stephen J. Klein, Cordova, both of Tenn.

[73] Assignee: Vollrath Group, Inc., Sheboygan, Wis.

[21] Appl. No.: 735,997

[22] Filed: Jul. 25, 1991

[51] Int. Cl.⁵ .................................................. B65D 69/00
[52] U.S. Cl. ................................... 206/571; 141/27; 206/364; 206/370; 206/438
[58] Field of Search ............... 206/363, 364, 365, 370, 206/570–572, 440, 518, 519, 520, 438; D7/317, 318; D9/383; 141/22–24, 25–27

[56] References Cited

U.S. PATENT DOCUMENTS

| | | | |
|---|---|---|---|
| 14,524 | 3/1856 | Stull | 141/23 X |
| D. 199,037 | 9/1964 | Jackson et al. | D7/318 X |
| D. 219,055 | 10/1970 | Borin | D7/317 |
| D. 287,806 | 1/1987 | Borin | D7/317 |
| 2,243,908 | 6/1941 | Kassab | 141/24 X |
| 2,541,065 | 2/1951 | Jabour | 215/1 C |
| 3,380,489 | 4/1968 | Harautuneian | 206/364 X |
| 4,925,047 | 5/1990 | Valentine et al. | 206/570 X |
| 4,936,448 | 6/1990 | Holloway | 206/364 |
| 4,954,239 | 9/1990 | Mueller | 206/571 |
| 5,072,832 | 12/1991 | Valentine et al. | 206/570 |

FOREIGN PATENT DOCUMENTS

| | | | |
|---|---|---|---|
| 64511 | 2/1941 | Norway | 206/520 |
| 1355121 | 5/1974 | United Kingdom | 206/520 |

OTHER PUBLICATIONS

Photographs of commercial water pitcher (views of side, front and bottom).

Primary Examiner—Bryon P. Gehman
Attorney, Agent, or Firm—Olson & Hierl, Ltd.

[57] ABSTRACT

Disclosed is a chambered irrigation container construction adapted for holding irrigation liquid for delivery to a wound site by irrigation syringe or by pouring, an irrigation unit comprising the container and sterilizable irrigation kit therefor. The open-top container comprises a bottom portion and a substantially upright sidewall extending upward therefrom so that a first portion defines a first chamber, a second portion defines a second chamber and a neck portion defines a flow channel placing each chamber in fluid flow communication with one another. The irrigation container is stabilized against sideways tipping by certain stabilizing features and is nestable with similar containers by certain nesting features. In a preferred embodiment the first portion defines an integral spout and the exterior surface of the second portion defines an integral gripping means which cooperates with the second chamber to prevent an irrigation syringe received therein from entry into the flow channel and first chamber.

20 Claims, 3 Drawing Sheets

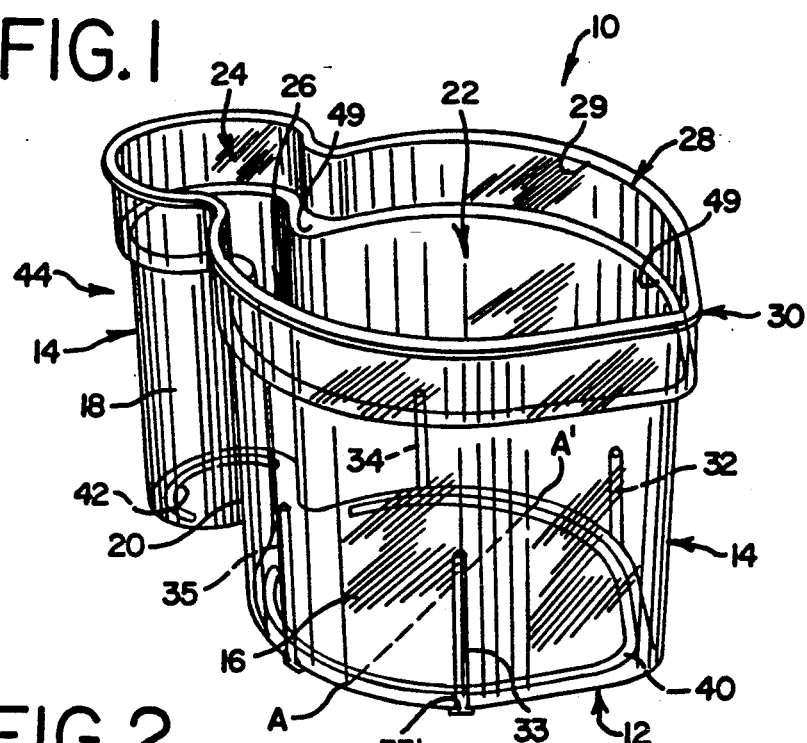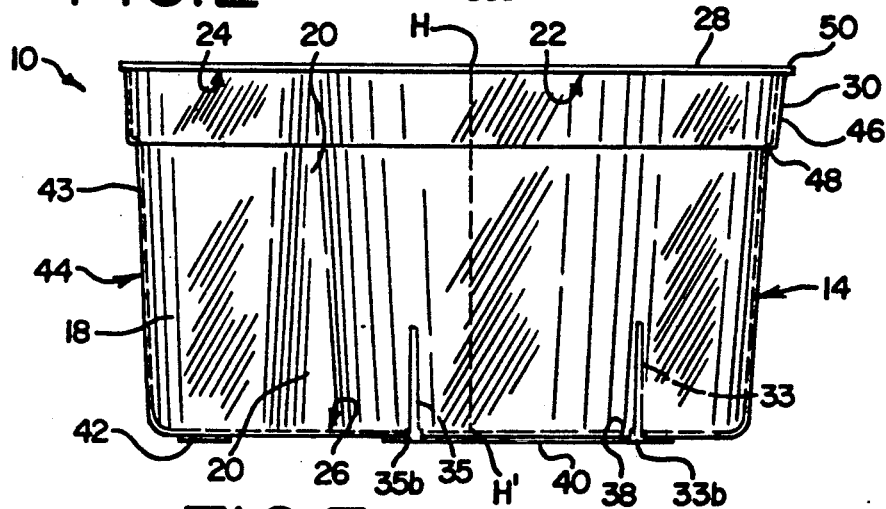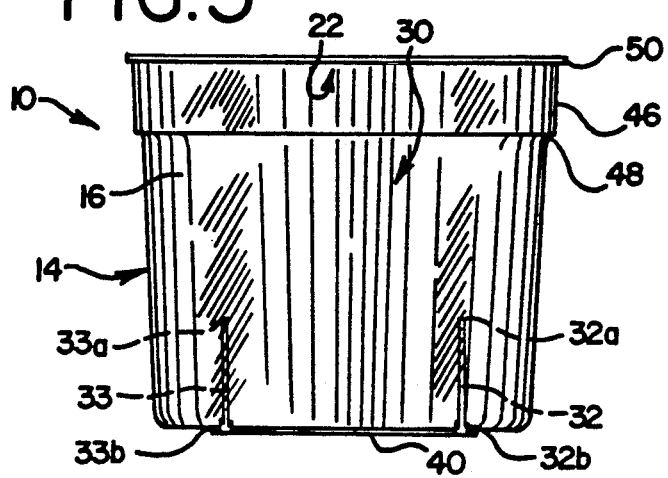

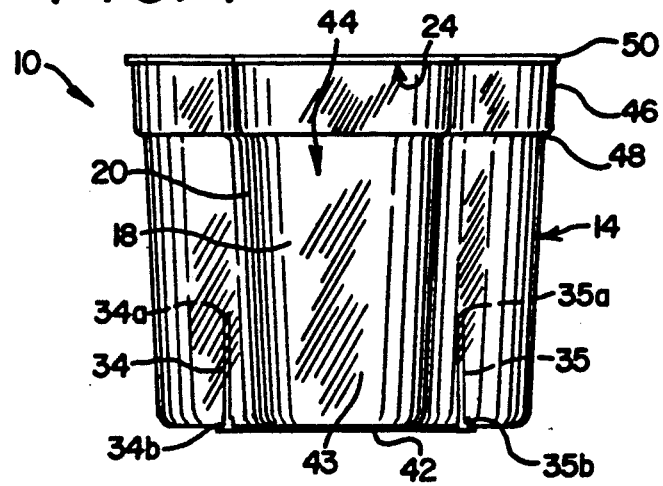
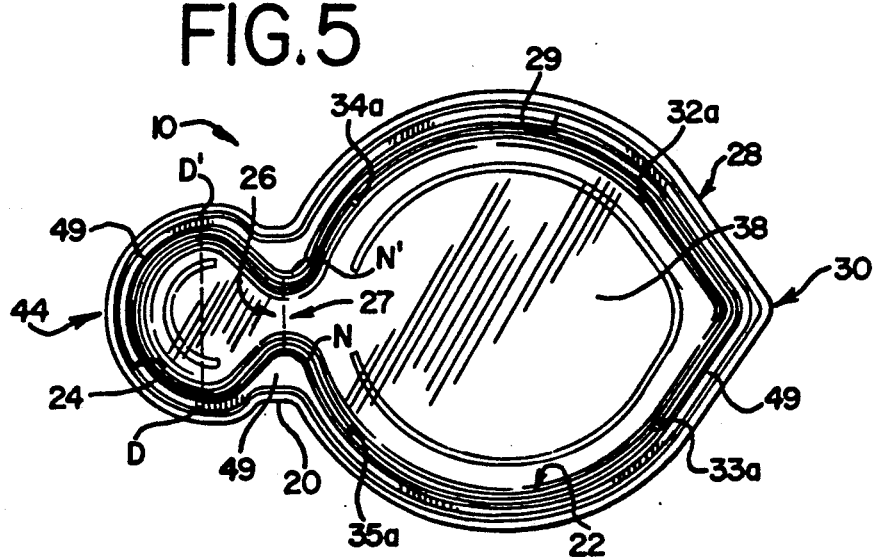
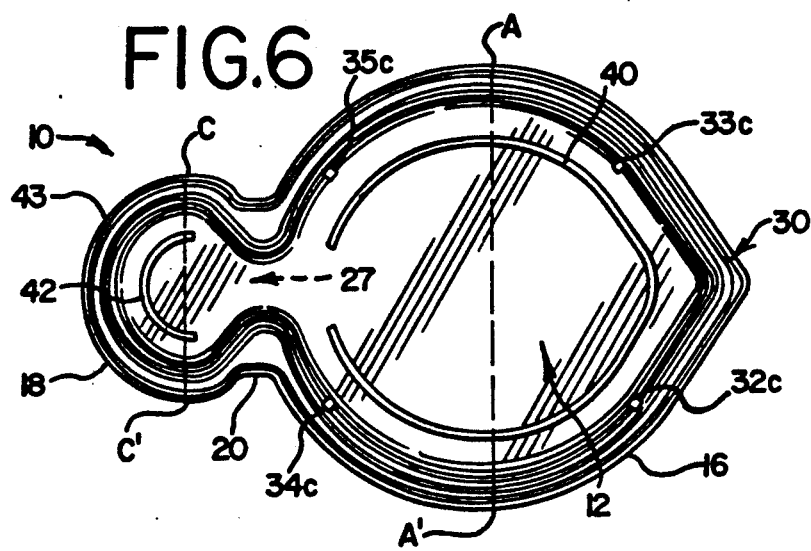

IRRIGATION CONTAINER AND SYRINGE

FIELD OF THE INVENTION

This invention relates to containers for holding irrigation liquid and in particular to a chambered irrigation container and unit for holding and delivering irrigation liquid.

BACKGROUND OF THE INVENTION

During the course of caring for patients, sterile irrigation water is commonly used to irrigate and cleanse incisions or open wound sites. In hospitals, this irrigation procedure can be performed in the operating room, in the emergency room or in the patient's hospital room. Alternatively, irrigation procedures may be performed in the doctor's office, ambulance or in first aid centers.

For this purpose, sterile liquid, such as irrigation water or saline, is generally supplied in sealed containers. Accordingly, it is desirable to have available irrigation kits comprising sterilizable utensils capable of holding and delivering this irrigation liquid to an incision or wound site. In certain instances, incisions or wound sites are preferably irrigated by pouring a relatively thin stream of liquid directly on the site.

Present irrigation containers are open wide-mouth bowls, basins or pitchers. In common surgical practice, umbilical ties and vascular loops are frequently draped on the open upper edge of these irrigation containers for ready access, particularly during the irrigation procedures. However, when an irrigation syringe is received in the container and is operated for withdrawing irrigation liquid, the syringe can accidentally also aspirate such tapes or loops. There is a need, therefore, for an irrigation container constructed to hold an irrigation syringe in a manner which avoids the foregoing problem while liquid is being withdrawn.

Irrigation containers frequently are combined with other surgical utensils for operating room kits and frequently are sealed for sterilization. A problem arises, however, when the height of the irrigation container exceeds the height of another kit item, such as a ring stand basin, causing a bulge which can result in tearing of the overwrapping and break the sterile seal. A bulge also limits the number of kits which can be placed in a sterilizer.

Desirably, an irrigation container is formed of sterilizable plastic and is nestable for convenient stacking storage. However, when plastic containers are nested, the sidewalls of one container tend to fictionally interlock with the sidewall of another making separation of individual containers difficult.

Accordingly what is needed, therefore, is an irrigation container which offers the benefits of a lipless reservoir for holding irrigation liquid from which a desired amount can be withdrawn by an irrigation syringe for delivery to a wound site and that of a spouted pouring container for delivering a relatively narrow stream of irrigation liquid directly to an incision or wound site. Moreover, an ideal irrigation container should also be stabilized against sideways tipping and suited for use in sterilizable irrigation units and kits.

The irrigation container of the present invention overcomes the foregoing problems and meets the desired needs.

SUMMARY OF THE INVENTION

A two-chambered open-top irrigation container construction is disclosed having certain stabilizing and nesting features. The container is adapted for holding irrigation liquid for delivery to an incision or wound site by irrigation syringe or by pouring. An irrigation unit suited for use in a sterilizable irrigation kit comprising the container of this invention is also disclosed.

Briefly described, a preferred embodiment of an irrigation container embodying the principles of this invention comprises an open-top container stabilized against sideways tipping, having an integral gripping means and two chambers in liquid flow communication with one another. One of the two chambers is dimensioned to cooperate with the gripping means to hold an irrigation syringe during an irrigation procedure and the other chamber is preferably larger and has an integral pronounced spout adapted for delivering a relatively narrow stream of irrigation liquid. To stabilize the container against sideways tipping, the angular relationship of the sidewall of the container to the flat bottom portion is about perpendicular and the height of the sidewall, as defined from its upper edge to the bottom portion, is about equal to the exterior diameter of the larger chamber.

Specifically, the irrigation container comprises a generally flat bottom portion and a substantially upright sidewall extending upward from the bottom portion. The sidewall includes a first portion which defines a first chamber, a second portion which defines a second chamber, and a neck portion which defines a flow channel between the first and second chambers to place them in fluid flow communication with one another. The sidewall terminates in an upper edge extending about the first portion, second portion and neck portion of the container to define an opening to the top of the container to be in fluid communication with the first chamber, second chamber and flow channel.

One preferred container embodiment includes an integral spout defined by the upper edge of the first portion adapted to deliver a relatively narrow stream of liquid when irrigation liquid is placed in the first chamber, the exterior surface of the second portion defines an integral gripping means, and the exterior diameter of the first chamber is larger than that of the second chamber.

In a preferred irrigation unit embodiment an irrigation syringe having a barrel body diameter smaller than the second chamber and a height greater than the height of the sidewall of the container can be received in the second chamber for withdrawing liquid and yet be kept separated from entering the flow channel and first chamber. Additionally the irrigation syringe can be held within the second chamber when not in use. A preferred kit embodiment includes a basin having a height and diameter adapted to retain an irrigation container embodiment of this invention and an irrigation syringe releasably sealed side by side therein without substantial overwrap bulge.

The disclosed container provides the combined benefits of a reservoir offered by the second chamber holding liquid for withdrawal by irrigation syringe and a spouted vessel by the first chamber holding liquid for delivery to a wound site by pouring. A particular benefit is the sideways stability of the container and the integral gripping means provided by the exterior wall of the second chamber. Another particular benefit is the cooperation of the second chamber with the integral gripping means to hold an irrigation syringe therein without tipping the container sideways, and especially to prevent entry of the syringe into the flow channel and the first chamber so that surgical tapes and umbilical ties can be draped on the edge of the first chamber without being aspirated by the irrigation syringe when irrigation liquid is withdrawn.

Numerous other features and advantages of the present invention will become readily apparent from the following detailed description of the invention, the accompanying drawings and the appended claims.

BRIEF DESCRIPTION OF THE DRAWINGS

FIG. 1 is a perspective view of a preferred embodiment of a two-chambered open-top irrigation container of this invention showing the relationship of the first chamber defined by the first portion, the second chamber defined by the second portion, and the flow channel defined by neck portion of the sidewall to the bottom portion and the relationship of the interior and exterior lug means;

FIG. 2 is a side elevational view of the container embodiment seen in FIG. 1;

FIG. 3 is a front elevational view of the container embodiment seen in FIG. 1 showing the integral spout formed by the first portion;

FIG. 4 is a rear elevational view of the second portion and integral gripping means of the container embodiment seen in FIG. 1;

FIG. 5 is a view of the top portion of the container embodiment seen in FIG. 1;

FIG. 6 is a view of the bottom portion of the container embodiment seen in FIG. 1;

DETAILED DESCRIPTION OF A PREFERRED EMBODIMENT

Figure 7:
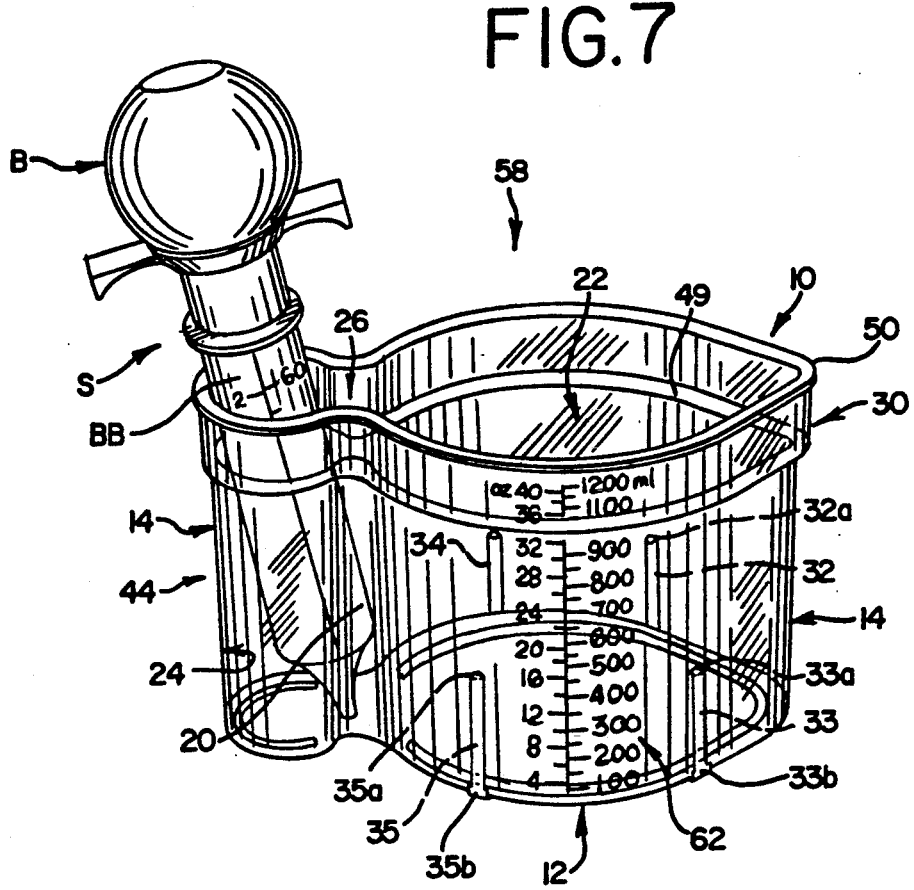
FIG. 7 is a perspective side view of an irrigation unit embodiment of this invention with the second chamber receiving and holding an irrigation syringe therein.

Referring to FIGS. 1–8, an irrigation container in accordance with the present invention is designated generally by the reference numeral 10. The container 10 includes a generally flat bottom portion 12 and a substantially upright sidewall 14 extending upward from the bottom portion 12 in generally perpendicular relationship to the bottom portion 12 (as best seen in FIGS. 1–4 and 7).

As seen in FIG. 1, the container 10 comprises a generally flat bottom portion 12 and a substantially upright sidewall 14. The sidewall 14 includes the first portion 16, a second portion 18 and a neck portion 20 and terminates in an upper edge 28. The first portion 16 defines a first chamber 22 and the second portion 18 defines a second chamber 24 which are placed in fluid communication with each other by a flow channel 26 which is defined by the neck portion 20. An opening 29 is defined by the upper edge 28. The opening 29, the first chamber 22, the second chamber 24 and the flow channel 26 are all in fluid communication with each other as seen in FIGS. 1, 5 and 7.

As illustrated in FIG. 1, an integral spout 30 is defined by the upper edge 28 of the first portion 16. The spout 30 preferably cooperates with the bottom portion 12 to form a substantially pronounced spout 30 (best seen in FIGS. 1, 2, 5 and 6) to deliver irrigation liquid in a relatively narrow stream when liquid is placed in the first chamber 22 and pouring irrigation practiced. A benefit of the pronounced spout 30 is that incisions and wound sites can be irrigated by pouring a relatively narrow stream of liquid directly from the first chamber 22. The formation of the integral spout 30 by the first portion 16 is seen in the front view of the container shown in FIG. 3 in particular.

The second portion 18 of the sidewall 14 defines a lipless second chamber 24 which is placed in fluid communication with first chamber 22 by the flow channel 26. The flow channel 26 is defined by the neck portion 20. In the preferred container embodiment, the interior surface of sidewall 14 cooperates with the neck portion 20 to define open flow channel 26 to preferably extend from the upper edge 28 to the bottom portion 12 so that the opening 27 of the flow channel 26 is substantially equal to the interior width N—N' (shown in FIG. 5) of the neck portion 20. A continuously open flow channel is preferred for unrestricted flow communication of irrigation liquid (not shown) between the first chamber 22 and the second chamber 24 when liquid is placed in container 10. Alternatively the flow channel 26 can be an opening positioned towards the interior bottom portion of the container 10, so long as when irrigation liquid is present in the first chamber 22, it can easily flow into the second chamber 24 to be held therein for withdrawal by an irrigation syringe S received in chamber 24 as illustrated in FIG. 7.

In the preferred container embodiment, the diameter (A—A' shown in FIGS. 1 and 6) of the first chamber 22 is larger than the diameter of the second chamber (shown as C—C' in FIG. 6) so that the exterior surface 43 of the second portion 18 defines a gripping means 44 for hand holding the container 10. The gripping means 44 is best seen in FIGS. 1, 2, 4, 5, 6 and 7. In a preferred embodiment of a container embodying the gripping means principles of this invention, the exterior surface of the neck portion 20 further provides symmetrically opposing thumb and finger rests regardless of whether the container 10 is held in the right hand or the left hand. For this purpose, the second chamber 24 is preferably configured in semi-cylindrical form with the exterior surface 43 of the gripping means 44 symmetrically angled inwardly toward the neck portion 20 at about 45 degrees from the longitudinal center line of the container 10.

Moreover, the integral gripping means 44 also enhances the strength and stability of the container 10 and cooperates with the second chamber 24 during irrigation practice to either receive or to hold an irrigation syringe S (shown in FIGS. 7–8) respectively, when the syringe is in use and not in use. The second chamber 24 preferably has an interior diameter (D—D', shown in FIG. 5) which is larger than the exterior diameter of the barrel body BB (shown in FIG. 7) of a conventional irrigation syringe having a liquid volume capacity of about 2 ounces to cooperatively receive the irrigation syringe S therein for withdrawing irrigation liquid and for holding the irrigation syringe S when it is not in use (as illustrated by Unit 58 in FIG. 7 to be discussed below). For this purpose, the second chamber 24 preferably is lipless to provide a reservoir of liquid and is configured to cooperate with the sidewall defining the flow channel to retain and hold the irrigation syringe S separate from entering the first chamber 22 and yet cooperate with the exterior surface 43 of the sidewall 14 to provide a comfortable gripping means 44.

The container 10 is stabilized against sideways tipping by the relationship of the height of the sidewall 14, as defined from the upper edge 28 to the bottom portion 12 (shown in FIG. 2 by H—H'), to be about equal to the exterior diameter A—A' shown in FIGS. 1 and 6 defined by the bottom portion 12 of the first chamber 22. A particularly preferred embodiment of container 10 has a height of about 4⅛ inch to about 4¼ inch (about 10.3 centimeters to about 10.6 centimeters). To further stabilize container 10 against sideways tipping, discontinuous stabilizing support means 40, 42 are disposed about the exterior surface of the bottom portion 12.

The configuration of the support means 40, 42 is not limited, but for ease and convenience of production, is preferably in the form of a discontinuous ring like structure which generally reflects the configuration of the chamber under which it is positioned. As best seen in FIGS. 1, 6 and 7, stabilizing support 40 can be in the form of an open elliptical rib positioned about the exterior bottom portion 12 of the first chamber 22 and stabilizing support 42 can be in the form of a semi-circular rib positioned about the exterior surface of the bottom portion 12 of the second chamber 24 with no support means on the bottom portion 12 of the neck portion 20 but is not so limited. The discontinuous support means avoids hydroplaning of the container 10 when it is placed on a wet surface. The stabilizing support means is preferably integrally formed with the container 10. A satisfactory ring-like support can be about 0.04 inches (about 0.1 centimeters) in height and about 0.06 inches (about 0.15 centimeters) in width but is not so limited.

The sidewall 14 of the container 10 also extends upward and is generally perpendicular to the bottom portion 12 to further provide maximum sideways stability. However, for practical reasons and convenience in stackable storage and shipping, the container 10 is preferably nestable inside another like container 10. For this purpose, a plurality of interior lug means 32-35 and corresponding cooperative exterior lug means 32b, 33b, 34b, 35b are included (best seen in FIGS. 1-7), which cooperate to limit the extent to which identical containers can be nested one inside another. Additionally these lug means maintain the bottom portion of two containers in a parallel spaced relationship with an air space therebetween to avoid interlocking of the container by friction fit or vacuum seal.

Satisfactory results can be obtained with four lug means as illustrated in FIGS. 1 and 7 with the interior lug means 32-35 being disposed on the interior surface 36 of the sidewall 14 of the first chamber 22 each lug means being in the form of a rib which extends upwardly and projects inwardly from the bottom portion 38 and is of equal height. Each interior lug means terminates in a substantially flat ledge, 32a, 33a, 34a and 35a, which has sufficient width to abut and seat with corresponding exterior lug means, 32b, 33b, 34b and 35b, in the form of a rib disposed on the exterior surface 43 of the sidewall 14 of a second container. The exterior lug means extend downward from the first portion 16 and each is positioned where the sidewall 14 meets the bottom portion 12 and terminates in a generally flat lower edge, 32c, 33c, 34c, 35c which is substantially parallel to the bottom of the container.

The interior lug means 32-35 illustrated in FIGS. 1-7 are preferably positioned in circumferentially spaced relation about the interior surface 36 of the sidewall of the first chamber 22. As best seen in FIGS. 5-6 interior lug means 32, 33 and exterior lug means 32b, 33b are each symmetrically positioned equidistant from one another at about 39 degrees from the longitudinal center line and adjacent the spout 30, with interior lug means 34, 35 and exterior lug means 34b, 35b symmetrically positioned at about 39 degrees from the longitudinal center line and adjacent the neck portion 20, but are not so limited.

Satisfactory nesting results are obtained with interior lug means 32-35 each having a width of about 0.059 inches (about 0.15 centimeters), a corresponding ledge 32a, 33a, 34a, 35a having an inward width of about 0.08 inches (about 0.2 centimeters) an inward taper of about 0.5 degrees from parallel and a length of about 1.2 inches (about 3 centimeters) as defined from the ledge to the interior surface of the bottom portion 38 of the first chamber 22. Satisfactory results can be obtained with exterior lug means, 32b 33b, 34b, 35b each having a width of about 0.125 inches (about 0.3 centimeters) and a flat lower edge, 32c, 33c, 34c, 35c, substantially equal to the width of the interior edges.

By the cooperation of each ledge of an interior lug means and a corresponding lower edge of an exterior lug means, for example, 32a with 32c, container 10 can be nested with a like container keeping the bottom portions of each container in parallel spaced relationship with an air space therebetween. This nesting feature avoids interlocking of the sidewalls of each container with one another by friction fit and avoids a vacuum seal. The relationship of the interior ledge to the exterior lower edge of each lug means diminishes the likelihood of cocking of one container inside another and facilitates separation of nested or stacked containers.

In the preferred container embodiment, the upper edge 28 including the sidewall 14 towards the top of the container 10 is stepped outwardly and generally parallel to the bottom portion 12 to form a collar 46 and step 48 on the exterior surface of the sidewall 14. The upper edge 28 is also provided with a rim 50. Where the interior surface 36 of the sidewall 14 meets the collar 46, interior shoulder 49 is provided (best seen in FIGS. 1, 5 and 7). A useful rim 50 can be about 0.05 inches (about 0.1 centimeters) in height and about 0.1 inch (about 0.2 centimeters) in width and a useful step 48 can be about 0.01 inch (about 0.02 centimeters).

The collar 46, step 48 and rim 50 provide strength to the opening 29 of the container 10. For this purpose, the height of the collar 46, defined from a point on the rim 50 to where the collar 46 meets the step 48, is preferably about 0.9 inches (about 2.2 cm.) and has a wall thickness of about 0.055 inches (about 0.1 centimeters). Otherwise, the width of the sidewall 14 can be about 0.04 inches (about 0.1 centimeters) to about 0.05 inches (about 0.125 centimeters).

For ease in stacking storage of a container of this invention, the sidewall 14 can be tapered inwardly to about 3 degrees from parallel and the collar 46 can be tapered inwardly to about 1 degree from parallel so that the opening 29 is wide enough to receive the bottom of another container 10 of like shape for nesting purposes.

During irrigation practice umbilical ties and vascular loops can be draped on the edge of the container 10 and supported by the rim 50 and the shoulder 49 in the unit 58 illustrated in FIG. 7 without being aspirated when the irrigation syringe S is activated for withdrawing liquid (not shown) when liquid is present in the container 10.

The step 48 additionally provides additional hand and finger support to the gripping means 44 and assists in preventing the container 10 from slipping during irrigation practice, especially pouring practice. To further assist in handling the container 10 and in providing support for the gripping means 44, the width of the step is preferably greater at the neck portion 20. This increased width also provides an increase in the radial width of the shoulder 49 at the neck portion 20 of the sidewall 14 and cooperates in defining the opening 27 of the flow channel 26 to a width substantially equal to the width N—N' of the neck portion 20. This feature is best seen in the preferred embodiment shown in FIGS. 1, 5, 6 and 7.

An irrigation unit 58 embodying the principles of this invention is illustrated in FIG. 7 with an irrigation syringe S shown received in the second chamber 24 and separately held therein from contact with the flow channel 26 and first chamber 22.

Figure 8:
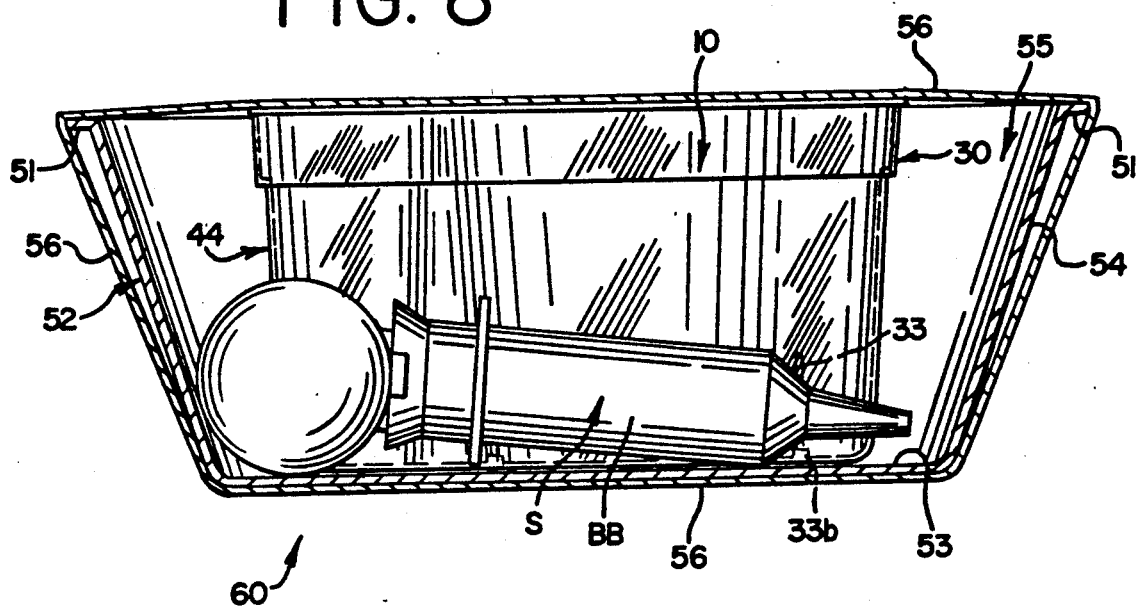
FIG. 8 is a side elevational view of a preferred irrigation kit comprising an irrigation container embodying the principles of this invention received side by side with an irrigation syringe in an irrigation basin and releasably sealed for sterilization.

In conventional irrigation practice, it is desirable to use an irrigation syringe S with a barrel body BB having a volume capacity of about 50 cubic centimeters to about 60 cubic centimeters or approximately 2 ounces as shown in FIGS. 7 and 8. The irrigation syringe S is typically fitted with a flexible bulb B to assist in withdrawing liquid (not shown), when liquid is present in container 10. The irrigation syringe S, therefore, has an exterior barrel body diameter smaller than the interior diameter (D—D' shown in FIG. 5) of the second chamber 24 but greater than the width (N-N' shown in FIG. 5) of the neck portion 20, so that the barrel body BB is held within the second chamber 24. The height of the syringe S is also greater than the height of the sidewall 14, as defined from the upper edge 28 to the bottom portion 12, (illustrated by H—H' in FIG. 2).

In the unit embodiment of this invention, the second chamber 24 is, in effect, a lipless reservoir from which liquid can be withdrawn by an irrigation syringe S and which can also hold the irrigation syringe S without sideways tipping of the container when the syringe S is not in use. As shown by the alternative container embodiment in FIG. 7, fluid volume measuring indicia 62 can be disposed on at least one interior or exterior surface of the sidewall 14 preferably on the surface of the first portion 16 positioned transverse to the spout 30. Preferably a pair of opposing indicia 62 are symmetrically disposed on each interior surface 36 of the sidewall 14 of the first portion 16 of the first chamber 22 so that fluid volume can be viewed from either left or right. Desirably the fluid volume capacity of container 10 is about 1300 cubic centimeters without the irrigation syringe S and has liquid indicia graduated for at least about 1200 cubic centimeters and about 40 ounces.

An irrigation container embodying the principles of this invention can be constructed by generally known manufacturing operations, such as injection molding, blow molding, drawing and the like. Molding is particularly preferred to integrally form the container.

The irrigation container 10 of this invention is preferably constructed of suitable material which is non-toxic to humans, relatively rigid and easily sterilizable with ethylene oxide gas and is desirably stable to cobalt 60 gamma radiation. Particularly preferred is a moldable plastic material, particularly one suited for molding operations. Exemplary materials are polymeric plastics, such as polypropylene, polyethylene, polyvinylchloride, polyethyleneterephthalate (PET), acrylic plastic and the like. Translucent clarified polypropylene is particularly preferred.

For irrigation practice, an open-top ring stand basin is commonly used. The irrigation container illustrated in FIGS. 1-6 and especially the irrigation unit illustrated in FIG. 7 is suited for use cooperatively with an irrigation basin 52 (shown in cross section in FIG. 8).

An irrigation container of the type shown in FIGS. 1-6 can be any overall dimension desired. However, a particularly useful container embodiment for use in an irrigation unit and kit embodying the principles of this invention, as illustrated in FIGS. 7 and 8, preferably has a sidewall height of about 4⅛ inches to about 4¼ inches (about 10.3 centimeters to about 10.6 centimeters) and an overall exterior dimension comprising a longitudinal axial length defined from an outside point of the first chamber to an outside point of the second chamber of about 7 inches to about 7.5 inches (about 17.5 centimeters to about 18.8 centimeters). The exterior diameter at the bottom portion of the first chamber (A—A', FIG. 6) when measured transverse to the longitudinal axis is preferably about equal to the sidewall height. Preferably, the diameter at the bottom portion of the second chamber (C—C', FIG. 6), when similarly measured is about 1.5 inches to about 1.75 inches (about 3.8 centimeters to about 4.4 centimeters); with the diameter at the top portion (D—D', FIG. 5) being about 2.5 inches (about 6.2 centimeters) to about 2.25 inches (about 5.6 centimeters) and the width (N—N', FIG. 5) of the flow channel being about 0.5 inches to about 0.75 inches (about 1.2 centimeters to about 1.9 centimeters). Preferably, container 10 is integrally formed with all its preferred elements as illustrated in FIG. 7.

A suitable basin 52 has a sidewall 54 about equal in height to the height (H—H', FIG. 2) of the sidewall 14 of container 10, an open upper edge 55, a rim 51 and a substantially flat bottom portion 53. The bottom portion 53 has an interior diameter greater than the overall exterior longitudinal dimension of container 10 to releasably receive unit 58 with container 10 positioned upright and in side-by-side relationship the irrigation syringe S as illustrated in FIG. 8.

Turning to FIG. 8, the benefit of the height of the container 10 also allows it to be prepackaged into a sterilizable irrigation kit 60 with the irrigation syringe S received in side-by-side sealed relationship within irrigation basin 52, for convenient packing into the sterilizer. For shipping purposes, sealing means 56 can be disposed about the open edge 55, rim 51, sidewall 54 and bottom 53 of the basin 52 to releasably seal the container 10 and syringe S therein without causing an overwrap bulge of kit 60. This minimizes accidental tears which can break the sterile seal and contaminate the kit items.

The preferred container embodiment illustrated in FIGS. 1-6 provide distinct advantages during irrigation usage, sterilization and stackable storage and is suited for use in an irrigation unit. The height of container 10 also allows it to be combined and packaged in a kit form with a ring stand basin without extending above the rim of the basin which thereby minimizes accidental tearing of sealing overwrap and allows easy combining with other operating room kit components. Additionally, a container and unit of this invention is sterilizable and disposable.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. An irrigation unit adapted for holding and delivering irrigation liquid, the unit comprising:
   (i) an irrigation syringe comprising a barrel body; and
   (ii) an irrigation container comprising:
      (a) a generally flat bottom portion;
      (b) a substantially upright sidewall extending upward from the bottom portion and including a first portion defining a first chamber, a second portion defining a second chamber and a neck portion defining a flow channel between the first and second chambers with the second chamber having an interior diameter larger than the barrel body of the syringe, the sidewall terminating in an upper edge extending about the first portion, second portion and neck portion of the container and defining an opening to the top of the container, such that the opening, first chamber, second chamber and flow channel cooperate with each other when irrigation liquid is present to allow the liquid to flow between the first chamber and the second chamber; and
      the neck portion having a width smaller than the interior diameter of the second chamber and the exterior diameter of the barrel body of the irrigation syringe.

2. The unit of claim 1 wherein the second portion of the container cooperates with the neck portion to define an open flow channel having an opening extending from the upper edge o the bottom portion.

3. The unit of claim 1, wherein the first chamber of the container is larger in diameter than the diameter of the second chamber.

4. The unit of claim 1, wherein the second portion of the container defines a container-gripping means on its exterior surface.

5. The unit of claim 1, wherein the height of the sidewall of the container, as defined from the upper edge to the bottom portion, is about equal to the exterior diameter of the first chamber to provide sideways stability to the container.

6. The unit of claim 1, wherein the syringe has a height greater than the height of the sidewall.

7. The unit of claim 1 wherein the container includes a discontinuous container-stabilizing support means about the exterior surface of the bottom portion of the first chamber and the second chamber.

8. The unit of claim 1 releasably received in an open-top basin, the basin having a substantially flat bottom, a sidewall extending upward from the bottom and terminating in an upper edge including a rim, the sidewall having a height about equal to the height of the container, and an interior diameter larger than the exterior dimension of the container to receive the container.

9. The unit of claim 1 wherein the first portion of the container defines a spout configured to deliver a liquid in a relatively narrow stream when liquid is placed in the first chamber and poured, and discontinuous container-stabilizing support means are disposed about the exterior surface of the bottom portion of the first chamber and the second chamber.

10. A prepackaged irrigation kit comprising in releasably sealed relationship:
    (i) an irrigation syringe comprising a barrel body;
    (ii) an irrigation container comprising:
       (a) a generally flat bottom portion;
       (b) a substantially upright sidewall extending upward from the bottom portion and including a first portion defining a first chamber, a second portion defining a second chamber and a neck portion defining a flow channel between the first and second chambers with the second chamber having an interior diameter larger than the barrel body of the syringe, the sidewall terminating in an upper edge extending about the first portion, second portion and neck portion of the container and defining an opening to the top of the container, such that the opening, first chamber, second chamber and flow channel cooperate with each other when irrigation liquid is present to allow the liquid to flow between the first chamber and the second chamber; and
       the upper edge of the first portion defining a spout configured to deliver a liquid in a relatively narrow stream when liquid is placed in the first chamber and poured;
    (iii) a basin having an open upper edge including a rim, a substantially flat bottom and a sidewall extending upward from the bottom, the sidewall having a height about equal to the height of the sidewall of the container, and an interior diameter sufficiently greater than the overall exterior dimension of the container and syringe when the container and syringe are received therein with the container in an upright position and in side-by-side relationship with the syringe; and
    (iv) a sealing means about the basin to releasably seal the container and syringe received in side-by-side relationship.

11. The kit of claim 10 wherein the second portion of the container cooperates with the neck portion to define an open flow channel having an opening extending from the upper edge to the bottom portion, the opening being about equal to the width of the neck portion.

12. The kit of claim 10, wherein the first chamber of the container has a diameter larger in diameter than the diameter of the second chamber.

13. The kit of claim 10, wherein the second portion of the container defines a container gripping means on its exterior surface.

14. The kit of claim 10, wherein the height of the sidewall of the container, as defined from the upper edge to the bottom portion, is about equal to the exterior diameter of the first chamber to provide sideways stability to the container.

15. The kit of claim 10, wherein the syringe has a height greater than the height of the sidewall.

16. The kit of claim 10, wherein the second chamber of the container has an interior diameter larger than the barrel body of an irrigation syringe having a liquid volume capacity of about 50 cubic centimeters to about 60 cubic centimeters.

17. The kit of claim 10, wherein the neck portion of the container has a width smaller than the diameter of the second chamber and the diameter of the barrel body of the irrigation syringe.

18. The kit of claim 10 wherein the container includes a discontinuous container-stabilizing support means about the exterior surface of the bottom portion of the first chamber and the second chamber.

19. The kit of claim 10 wherein the kit is sterile.

20. An irrigation container adapted for holding and delivering irrigation liquid to a wound site, the container comprising:

(a) a generally flat bottom portion;

(b) a substantially upright sidewall extending upward from the bottom portion and including a first portion defining a first chamber, a second portion defining a second chamber, a neck portion defining a flow channel between the first and second chambers, the sidewall terminating in an upper edge extending about the first portion, second portion and neck portion of the container and defining an opening to the top of the container, the opening, first chamber, second chamber and flow channel cooperate with each other when irrigation liquid is present to allow the liquid to flow between the first chamber and the second chamber;

the upper edge of the first portion defining a spout configured to deliver a liquid in a relatively narrow stream when liquid is placed in the first chamber and poured;

the second portion defining a means for gripping on its exterior surface;

the first chamber being larger in diameter than the diameter of the second chamber;

the height of the sidewall, as defined from the upper edge to the bottom portion, being about equal to the exterior diameter of the first chamber to provide stability to the container against sideways tipping;

the second chamber having an interior diameter with the sidewall cooperating with an irrigation syringe received therein for withdrawing liquid from the second chamber, the syringe being larger in diameter than the width of the flow channel to prevent entry of the syringe into the first chamber from the second chamber.

* * * * *